(12) United States Patent  
Valtchev

(10) Patent No.: US 8,617,179 B2  
(45) Date of Patent: Dec. 31, 2013

(54) CONNECTION MECHANISM FOR A UTERINE MOBILIZER

(76) Inventor: Konstantin Lazarov Valtchev, Toronto (CA)

( * ) Notice: Subject to any disclaimer, the term of this patent is extended or adjusted under 35 U.S.C. 154(b) by 806 days.

(21) Appl. No.: 12/660,677

(22) Filed: Mar. 3, 2010

(65) Prior Publication Data

US 2010/0287757 A1 Nov. 18, 2010

(51) Int. Cl.
*B23P 11/00* (2006.01)

(52) U.S. Cl.
USPC .......................... 606/119; 29/525.01; 606/201

(58) Field of Classification Search
USPC .......... 29/592, 428, 525.01, 525.02; 606/119, 606/201
See application file for complete search history.

(56) References Cited

U.S. PATENT DOCUMENTS 5,562,679 A * 10/1996 Valtchev ........................ 606/119
2006/0241652 A1* 10/2006 Doll et al. ..................... 606/119

* cited by examiner

*Primary Examiner* — Peter DungBa Vo
*Assistant Examiner* — Azm Parvez
(74) *Attorney, Agent, or Firm* — Sturm & Fix LLP

(57) ABSTRACT

A new connecting mechanism for the Valtchev® uterine mobilizer, model VUM-6 having a straight tube with a locking wheel attached close to one end of the tube pivotally mounted in a housing of the space bar and maintained by a spring loaded pin in realizable way. The another end of the tube is attached to a piston pivotally mounted and maintained within a hole in the head of the uterine mobilizer via the tube engaging a connecting slot in the head, and adapted to be disassembled by first releasing the locking wheel of the tube from the space bar and second, by rotating the tube in a prescribed degree which will align the tube with the vertical slot allowing removal of the tube with attached piston from the head. The distal end of a rod is bended 15°, which allows retroversion of the head at the same degree.

16 Claims, 5 Drawing Sheets

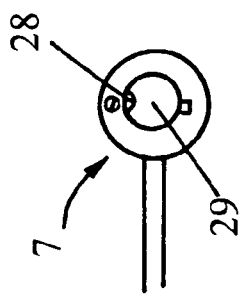
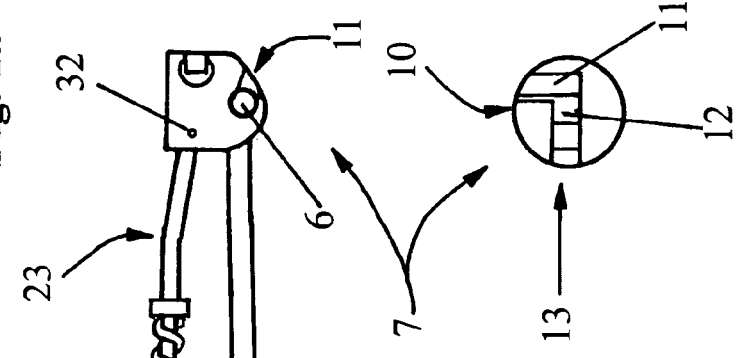

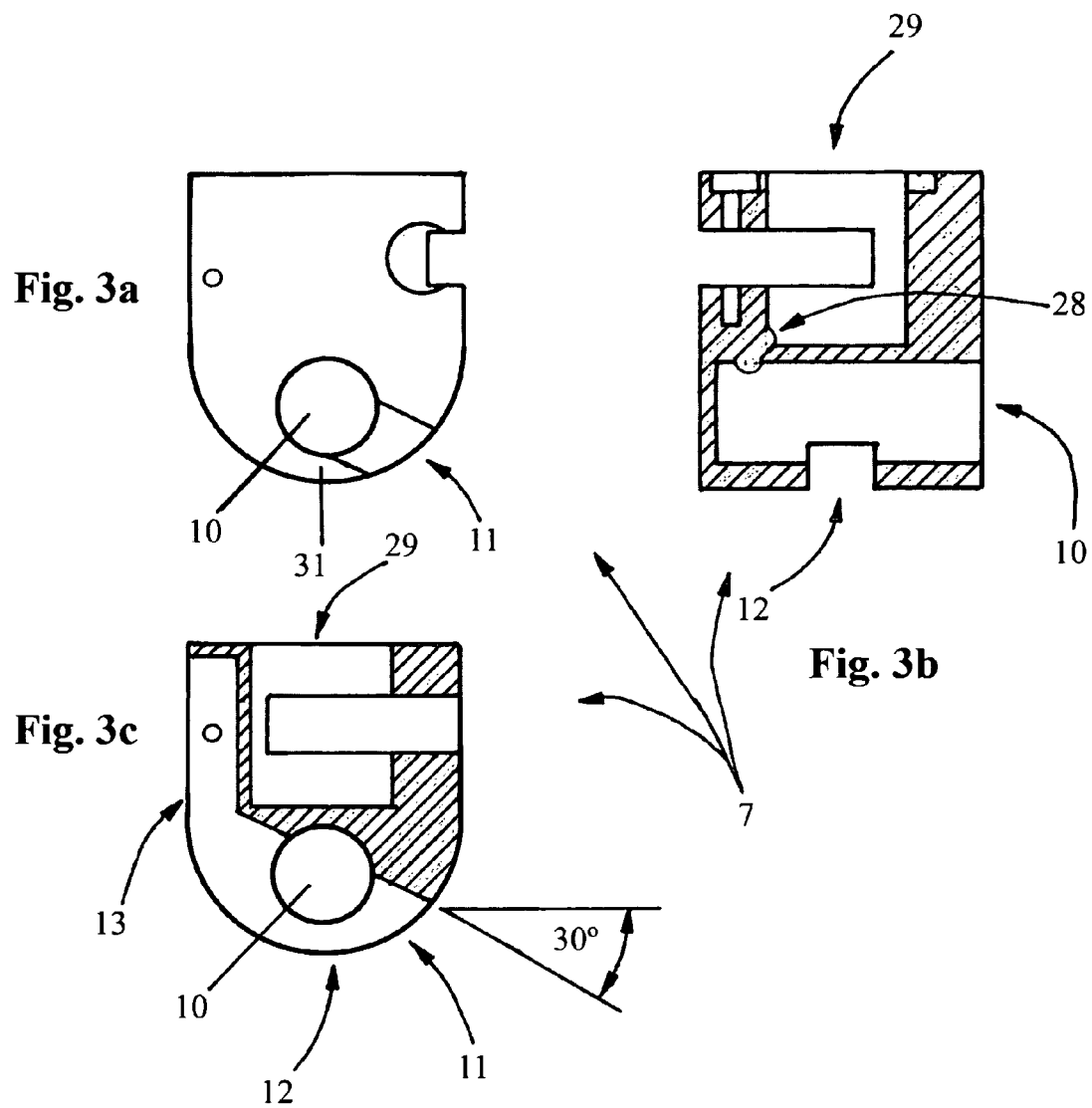

CONNECTION MECHANISM FOR A UTERINE MOBILIZER

This application claims the benefit of U.S. Ser. No. 08/321,062 filed Oct. 7, 1994 entitled "Connection Mechanisms for Uterine Mobilizer" by Konstantin L. Valtchev, now U.S. Pat. No. 5,445,643 issued Aug. 29, 1995 which is incorporated herein by reference.

BACKGROUND OF THE INVENTION

The present invention relates generally to a gynecological instrument necessary in gynecologic laparoscopy. More particularly, the present invention is directed to a uterine mobilizer or manipulator. Specifically the present invention is directed to an improved Valtchev® Uterine Mobilizer, model VUM-6, provided with new connecting mechanism for connecting the head of the uterine mobilizer to the space bar.

In my U.S. Pat. No. 5,445,643 the disclosure of which is incorporated by reference herein, I disclose and claim a gynecological instrument capable of mobilizing the uterus to any of its natural positions within the peritoneal cavity, which instrument lessens the danger of damage to the vaginal and uterine tissue and which instrument can be used for injection of dye into a uterus while the uterus is maintained in any of its natural positions. It was disclosed as well an improved connecting mechanism.

Extensive clinical experience with the previous model of the Valtchev® Uterine Mobilizer, model VUM-5, has shown that there is room for improvement of its connecting mechanism.

There have been reports of a disengagem of the tube from the tube holder and a leak of dye from the area of connection of the tube to the tube holder. Some users also mistakenly thought that the bent tube indicated a defect or that the tube had bent during transportation. It has been noticed as well, that the pin on the piston comes out of the slot during maximal anteversion and retroversion of the head. This allows disengagement of the piston from the head of VUM-5. This makes the mobilization of the uterus impossible. It was found, that the range of movement of the head of the model VUM-5 can be increased by about 15° by modification of the rod and the place of its attachment to the head.

The above mentioned shortcomings of the connecting mechanism of the Valtchev® Uterine Mobilizer, model VUM-5 has resulted in the necessity to invent a new connection mechanism for the next model, VUM-6 of the Valtvhev® Uterine Mobilizer.

Other objects, advantages and novel features of the present invention will become apparent from the following detailed description of the invention when considered in conjunction with the accompanying drawings.

BRIEF DESCRIPTION OF THE SEVERAL VIEWS OF THE DRAWINGS

FIG. 1a is a top plan view of the head of the Valtchev® Uterine Mobilizer, model VUM-6;

FIG. 1b is a side elevation view of the Valtchev® Uterine Mobilizer, model VUM-6

FIG. 1c is a bottom plan view of the head of the Valtchev® Uterine Mobilizer, model: VUM-6;

FIG. 3a is an exploded side elevation view of the head of the Valtchev® Uterine Mobilizer, model VUM-6;

FIG. 3b is an exploded longitudinal section view of the head of the Valtchev® Uterine Mobilizer, model VUM-6, along the axis of the hole;

FIG. 3c is an exploded longitudinal section view, across the hole of the head;

DETAILED DESCRIPTION OF THE INVENTION

Figure 2A:
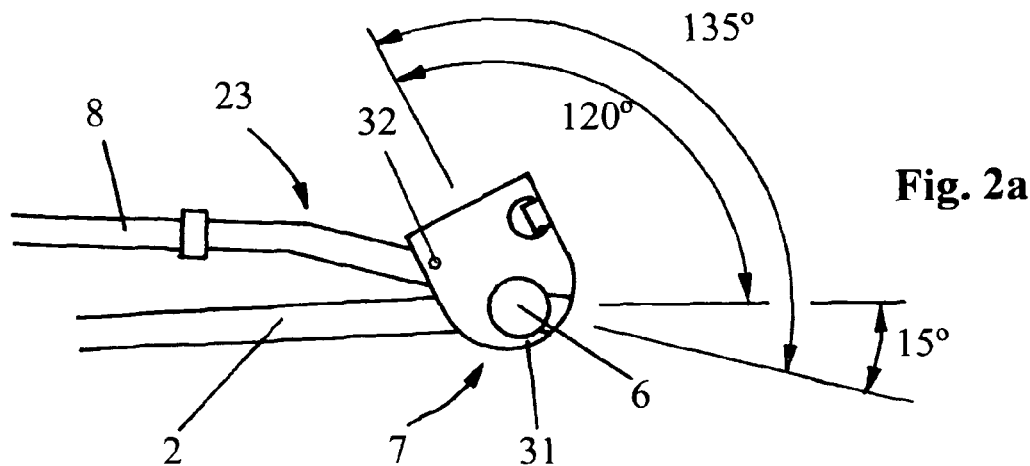
FIG. 2a is a side elevation view of the head of the Valtchev® Uterine Mobilizer, Model VUM-6, in maximal anteversion, at about 120'.
Figure 2B:
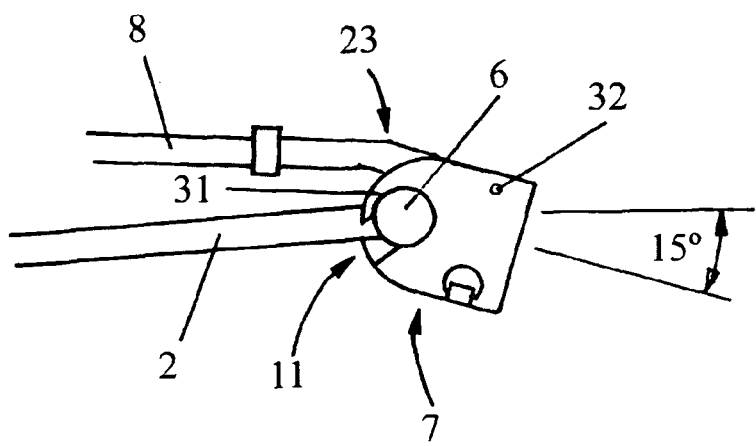
FIG. 2b is a side elevation view of the head of the Valtchev® Uterine Mobilizer in maximal retroversion, at about 15°.

The new connecting mechanism for Valtchev® Uterine Mobilizer, model. VUM-6 1, FIGS. 1a-1c consists of a straight tube 2 to which are permanently affixed a piston 6, a locking wheel 5 and a Luer lock 4. The tube of the previous model VUM-5 was bended in a bayonet profile, and was not directly attached to the space bar, by means of a tube holder. One end of a square rod 8, is pivotally attached by a pin 32, to a head 7 of the uterine mobilizer 1 and the opposite end of the rod 8 is pivotally attached by a pin 34 to a space bar 3. The end of the square rod 8 to which is attached the head has a bend 23. The rod is bended posteriorlly at 15°, which allows the head 7 to rotate 15° posteriorlly, increasing the range of movement from 120° of VUM-5 to 135° of VUM-6, FIGS. 2a and 2b. The rod of the previous model VUM-5 was straight. At the maximal retroversion at about 15°, the rod 8 reaches the bottom of the longitudinal slot 13 and can not rotate further. At maximal anteversion at about 120° of the head 7, the tube 2 reaches the bottom of the connecting slot, and can not rotate further.

There is a hole 10, FIGS. 3a-3c at the distal end of the head 7 of the uterine mobilizer, at 90° to a longitudinal slot 13 of the head 7. The hole 10 starts from one of the lateral walls of the head 7, and ends a few millimeters from the opposite lateral wall. At the bottom of the hole 10, from its proximal surface, starts an oblique canal 28, FIG. 3b, which opens into a cavity 29 of the head 7. The hole 10 accommodates the piston 7. There are three slots on the head 7, a vertical slot 11, a connecting slot 12 and a longitudinal slot 13. The vertical slot 11, and the connecting slot 12 communicate with the hole 10.

Figure 2C:
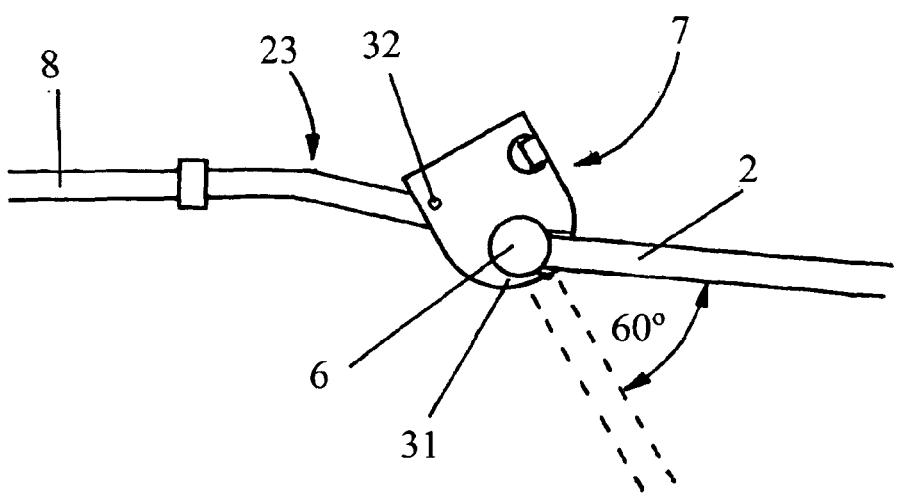
FIG. 2c is a side elevation view of the head of the Valtchev® Uterine Mobilizer, Model VUM-6, with inserted piston and a tube into the head at about 60° posteriorlly from the longitudinal axis of the head.

The longitudinal slot 13 starts a few millimeters from the proximal end of the head 7 and ends at the connecting slot 12. The axis of the longitudinal slot is perpendicular to the axis of the hole 10. A connecting slot 12 starts from the distal end of the longitudinal slot 13 and runs at about 30°, to the longitudinal axis of the head 7. FIG. 3c across the hole 10, and ends at the distal end of the vertical slot 11. The vertical slot 11 starts from the hole 10 and runs posteriorlly at about 60° from the longitudinal axis of the head 7 FIG. 2c.

Figure 4A:
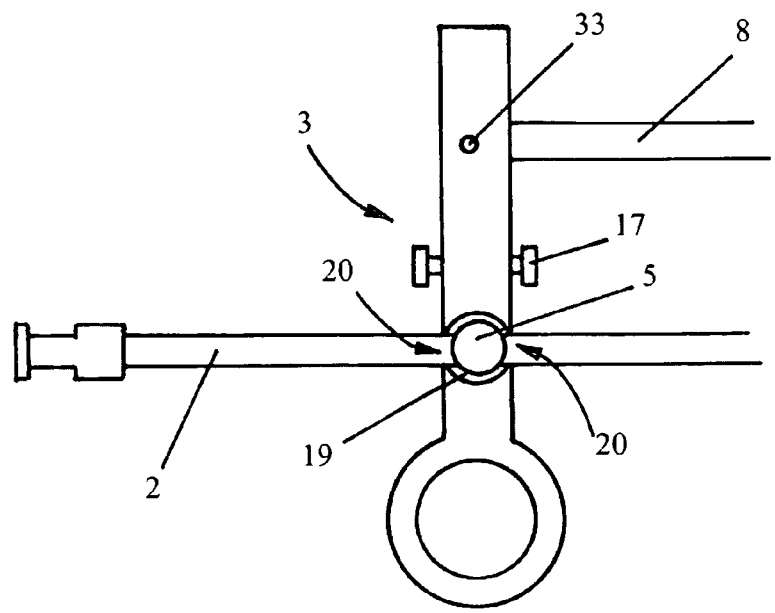
FIG. 4a is a side elevation view of the space bar.
Figure 4B:
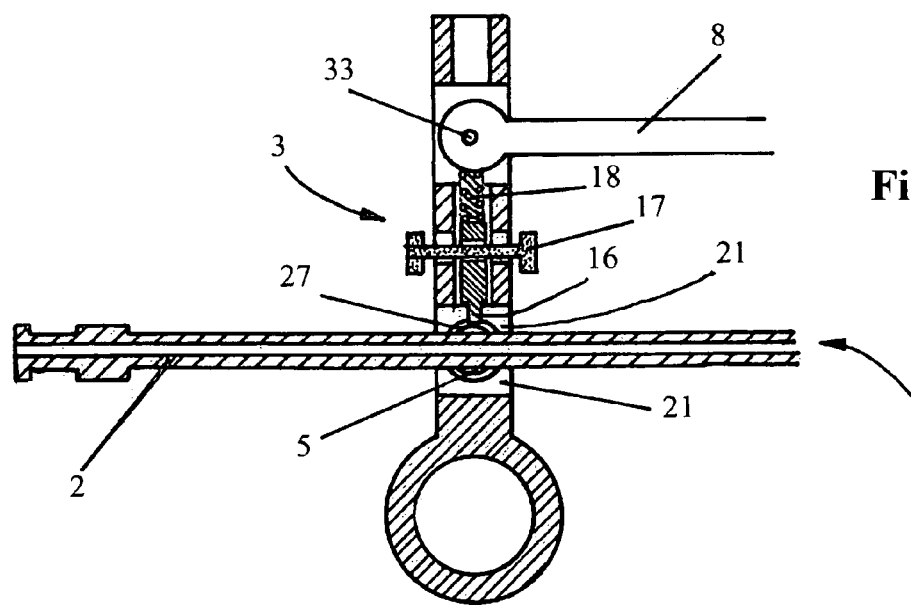
FIG. 4b is a side longitudinal section of the space bar.

The space bar 3, FIGS. 4a and 4b has a housing 19, accommodating the locking wheel 5 and the adjacent part of the tube 2. The locking wheel 5 and the adjacent part of the tube can be inserted into the housing 19 only if the tube is at 90° to the longitudinal axis of the space bar 3, aligned with the entrance 19 of the slot 21. The locking wheel 5, FIG. 5, has a canal 24 along one of its diameters through which the tube 2 is inserted and permanently affixed to the tube 2, about 5 cm from its proximal end. The Luer lock 4 is permanently affixed to the proximal end of the tube 2. A syringe can be attached to the Luer lock, for injection of fluids.

The distal end of the tube is permanently affixed to the piston in the middle of its length, at 90° to the longitudinal axis of the piston 6. The tube 2 of the previous model VUM-5 is permanently affixed to one end of the piston 6. The piston 6 has a canal 25 starting at its distal end, connected to a lumen 30 of the tube 2. At the distal end of the piston 6 on its outside surface, there is a groove 26 for mounting an "o" ring. The locking wheel 5 has a groove 27 around its circumference. The plane of the locking wheel 5 is at 90° to the longitudinal axis of the piston 6. The locking wheel 5 is pivotally held in a releasable manner by a spring 18 loaded pin 16, FIGS. 4a and 4b. By pulling a lever 17 proximally, the pin 16 releases the groove 27 of the locking wheel 5, and the locking wheel 5 and the tube can be removed from the housing 19, if the tube is aligned with the entrance 20 of the tube slot 21.

The novelty of the new connecting mechanism for VUM-6 can be understood better by describing its action. The piston 6 is inserted into the hole 10 and the tube 2 at about 60° into the vertical slot 11, until the tube reaches the bottom of the vertical slot 11, FIG. 2c. Then the tube 2 is pivoted on the piston 6 into the connecting slot 12 toward the longitudinal slot 13, FIG. 2c and FIG. 3c. As soon as the tube 2 enters the connecting slot 12, the tube 2 can not be removed, because the wall 31 of the connecting slot 12, is in its way, FIGS. 2a-2c. The next step is the insertion of the locking wheel 5 into its housing 19 on the space bar 3. Insertion of the locking wheel 5 into the housing 19 is possible only, if the tube 2 is at 90° to the longitudinal axis of the space bar 3, aligned with the entry 20 of a slot 21 of the space bar 3, FIGS. 4a and 4b. When the locking wheel 5 is entering the housing, the spring 18 loaded pin 16 enters the groove 27 of the locking wheel 5, preventing its release but allowing rotation of the locking wheel 5. After the tube 2 is pivotally attached to the head 7 and to the space bar 3, the uterine mobilizer is ready for use. By rotating the space bar 3, forward and backward, the head 7 of the uterine mobilizer can be rotated to about 135°, 15° of which are in retroversion. The range of movement of the head of VUM-5 was 120° and the head could not be retroverted. At the working range of 135° the tube 2 remains in the connecting slot 12 which makes the removal of the piston 7 and the attached to it tube 2 impossible. The piston 6 can be removed from the hole 10 only after the locking wheel 5 is disengaged and removed from the space bar 3 and is rotated about 60° posteriorlly, until the tube is aligned with the vertical slot 11, FIG. 2c, then it can be removed from the head 7.

Figure 5:
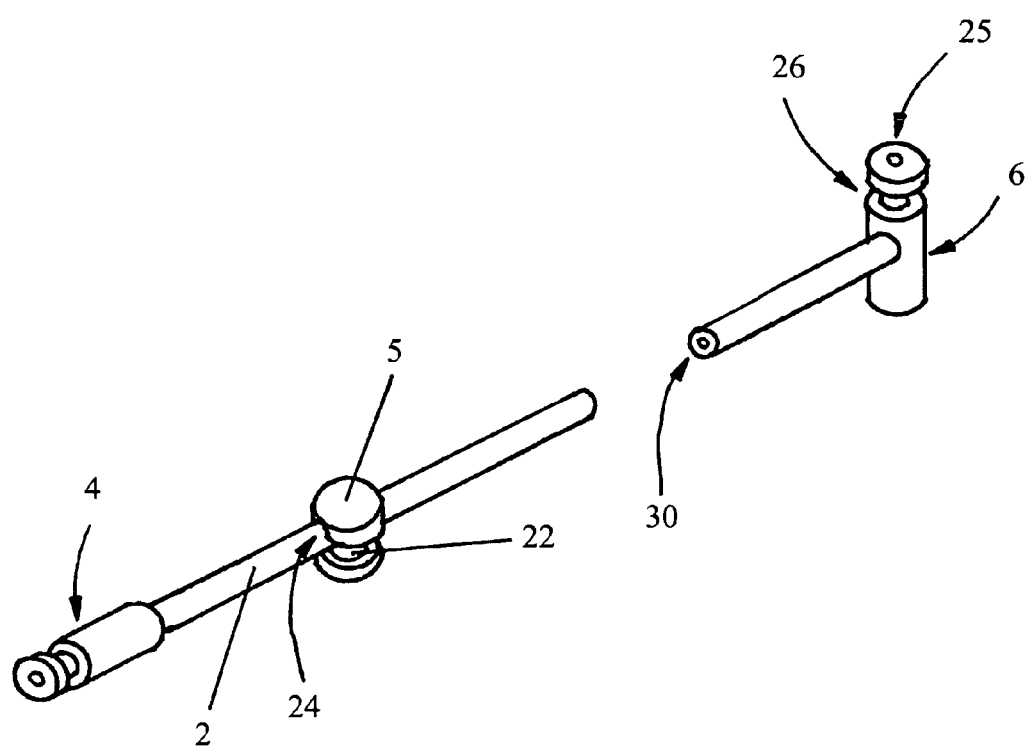
FIG. 5a is an oblique view of a tube with a permanently affixed piston, a locking wheel and a Luer lock.

When dye is injected through the Luer lock 4, the fluid runs into the lumen 30 of the tube 2, FIG. 4b and through the canal 25 of the piston 6, FIG. 5, 5, into the hole, pass through the oblique canal 28, FIG. 3b, and enters the cavity 29 of the head 7. The "o" ring, which is in the groove 26 on the piston, prevents leaking.

It is therefore apparent that many modifications and variations of the present invention are possible in the light of the above teaching. It is, therefore, to be practiced otherwise than as specifically described.

I claim:

1. A connection mechanism for a uterine mobilizer, comprising:
    a hollow tube with a locking wheel and a piston, connected in a pivotally releasable manner to a head of a uterine mobilizer and in a pivotally releasable manner to a space bar; and
    a rod pivotally attached by pins, one end to the head and the other end to a space bar, wherein, the tube is a straight, continuous tube having a proximal end and a distal end, the distal end being permanently affixed to the piston in a middle portion of said piston, and the locking wheel permanently affixed to said tube, closer to the proximal end of said tube; and
    wherein said tube is permanently affixed at 90° to a sidewall of the piston and is permanently affixed to a locking wheel having a plane at 90° to the longitudinal axis of said piston, the tube being connected in a pivotally releasable manner by said piston to a head of a uterine mobilizer, and the tube being connected in a pivotally releasable manner by said locking wheel to said space bar of a uterine mobilizer.

2. The connection mechanism for a uterine mobilizer of claim 1, wherein the piston includes a groove for installing an "O" ring, and a canal starting at one end of said piston connecting a lumen to said tube.

3. The connection mechanism for a uterine mobilizer of claim 1, wherein the locking wheel includes a circular groove at its periphery, a hole along one of its diameters and wherein the tube inserted through said hole and permanently affixed to said locking wheel.

4. The connection mechanism for a uterine mobilizer of claim 1, wherein the space bar includes a housing accommodating in a pivotally releasable manner said locking wheel, a spring loaded pin holding said locking wheel inside said housing and a lever by which said pin can be withdrawn, releasing said locking wheel.

5. The connection mechanism for a uterine mobilizer of claim 4, wherein said space bar additionally comprises an entrance to a tube slot, said tube can pass through, if said tube is perpendicular to the longitudinal axis of said space bar, a tube slot accommodating movements of said tube in a prescribed range, and a slot accommodating a rod pivotally attached to said rod by a pin.

6. The connection mechanism for a uterine mobilizer of claim 5, wherein said distal end of said tube is sliding into said connecting slot and cannot be disengaged during prescribed use.

7. The connection mechanism for a uterine mobilizer of claim 6, wherein said distal end of said tube and said connecting slot are adapted to be disengaged by rotating said tube about said piston by a prescribed degree of rotation.

8. The connection mechanism for a uterine mobilizer of claim 4, wherein said locking wheel pivots into said housing and is held in place by said spring loaded pin, engaging said groove of said locking wheel.

9. The connection mechanism for a uterine mobilizer of claim 8, wherein said locking wheel can be disengaged by withdrawing of said pin from said groove of said locking wheel.

10. The connection mechanism for a uterine mobilizer of claim 1, wherein said connecting mechanism comprises a passageway through a Luer lock, said tube, said piston, said hole, an oblique canal and opens into a head cavity.

11. The connection mechanism for a uterine mobilizer of claim 1, wherein a head of the uterine mobilizer comprises a hole accommodating a piston having an axis perpendicular to the longitudinal axis of said head, a longitudinal slot accommodating a rod pivotally attached by a pin to said head of the uterine mobilizer, a vertical slot connecting the said hole with the beginning of a connecting slot and a connecting slot connecting said vertical slot to said longitudinal slot.

12. The connection mechanism for a uterine mobilizer of claim 11 wherein the vertical slot starts from the hole and runs at 60° posteriorly from the longitudinal axis of said head, and exits on the surface of said head.

13. The connection mechanism for a uterine mobilizer of claim 1, wherein the rod has a distal end and a proximal end, the distal end is bent at 15° posteriorly, and pivotally attached to said head by said pin and the proximal end is pivotally attached by the pin to said space bar.

14. The connection mechanism for a uterine mobilizer of claim 1, wherein the connecting mechanism allows 120° anteversion of said head and about 15° retroversion of said head.

15. The connection mechanism for a uterine mobilizer of claim 14, wherein prescribed degree of ante version of said head is determined by reaching the bottom of said connecting slot by said tube.

16. The connection mechanism for a uterine mobilizer of claim 14, wherein the prescribed degree of retroversion of said head is determined by reaching the bottom of said longitudinal slot by said rod.

\* \* \* \* \*